United States Patent
Ablordeppey et al.

(10) Patent No.: US 11,129,831 B2
(45) Date of Patent: Sep. 28, 2021

(54) IDENTIFICATION OF AGENTS DISPLAYING FUNCTIONAL ACTIVATION OF DOPAMINE D2 AND D4 RECEPTORS

(71) Applicant: Florida A&M University, Tallahassee, FL (US)

(72) Inventors: Seth Y. Ablordeppey, Tallahassee, FL (US); Xue Y. Zhu, Tallahassee, FL (US)

(73) Assignee: Florida A&M University, Tallahassee, FL (US)

(*) Notice: Subject to any disclaimer, the term of this patent is extended or adjusted under 35 U.S.C. 154(b) by 0 days.

(21) Appl. No.: 16/537,193

(22) Filed: Aug. 9, 2019

(65) Prior Publication Data
US 2019/0365758 A1    Dec. 5, 2019

Related U.S. Application Data

(63) Continuation of application No. PCT/US2018/017600, filed on Feb. 9, 2018.

(60) Provisional application No. 62/457,491, filed on Feb. 10, 2017, provisional application No. 62/471,624, filed on Mar. 15, 2017.

(51) Int. Cl.
| | |
|---|---|
| *A61P 25/18* | (2006.01) |
| *A61K 31/496* | (2006.01) |
| *A61K 31/506* | (2006.01) |

(52) U.S. Cl.
CPC .......... *A61K 31/506* (2013.01); *A61K 31/496* (2013.01); *A61P 25/18* (2018.01)

(58) Field of Classification Search
None
See application file for complete search history.

(56) References Cited

U.S. PATENT DOCUMENTS

| | | | | |
|---|---|---|---|---|
| 5,034,390 | A * | 7/1991 | Olsson ................ | C07D 213/82 514/252.14 |
| 6,197,764 | B1 | 3/2001 | Bradley et al. | |
| 2002/0103105 | A1 | 8/2002 | Brioni et al. | |
| 2005/0192268 | A1 | 9/2005 | Ek et al. | |
| 2010/0029671 | A1 | 2/2010 | Tworowski et al. | |

OTHER PUBLICATIONS

Reagan-Shaw et al. "Dose Translation from Animal to Human Studies Revisited". FASEB J. 2007; 22:659-661. (Year: 2007).*
Jacob LS. Pharmacology (Fourth Edition). Williams and Wilkins. 1996. pp. 1-13. (Year: 1996).*
Peprah et al. "Multi-Receptor Drug Design: Haloperidol as a Scaffold for the Design and Synthesis of Atypical Antipsychotic Agents". Bioorganic & Medicinal Chemistry. 2012; 20:1291-1297. (Year: 2012).*
Allen et al., Discovery of beta-arrestin-biased dopamine D2 ligands for probing signal transduction pathways essential for antipsychotic efficacy. PNAS. 2011. vol. 108 (No. 45): 18488-18493.
Barnea et al., The genetic design of signaling cascades to record receptor activation. PNAS. 2008. vol. 105 (No. 1): 64-69.
Bricker et al., Evaluation of the behavioral and pharmacokinetic profile of SYA013, a homopiperazine analog of haloperidol in rats. Pharm Biochem Beh. 2012. vol. 102: 294-301.
Depoortere et al., F15063, a compound with D2/D3 antagonist, 5-HT1A agonist and D4 partial agonist properties: (II) Activity in models of positive symptoms of schizophrenia. Br J Pharmacol. 2007. vol. 151: 253-265.
Peprah et al. Multi-receptor drug design: Haloperidol as a scaffold for the design and synthesis of atypical antipsychotic agents. Bioorg Med Chem. 2012. vol. 20: 1291-1297.
Kleven et al., Novel antipsychotic agents with 5-HT1A agonist properties: Role of 5-HT1A receptor activation in attenuation of catalepsy induction in rats. Neuropharmacology. 2005. vol. 49: 135-143.
McCreary et al., SLV313 (1-(2,3-DihydroBenzo[1,4]-Dioxin-5-yl)-4-[5-(4-Fluoro-Phenyl)-Pyridin-3-ylmethyl]-PiperazineMonohydrochloride): A Novel Dopamine D2 Receptor Antagonist and 5-HT1A Receptor Agonist Potential Antipsychotic Drug. Neuropsychopharmacology. 2007. vol. 32: 78-94.
Needham et al., Zotepine: Preclinical Tests Predict Antipsychotic Efficacy and an Atypical Profile. Psychopharmacol Bull. 1996. vol. 32 (No. 1): 123-128.
Protais et al., Climbing Behavior Induced by Apomorphine in Mice: a Simple Test for the Study of Dopamine Receptors in Striatum. Psychopharmacology. 1976. vol. 50: 1-6.

(Continued)

*Primary Examiner* — Leslie A. Royds Draper
(74) *Attorney, Agent, or Firm* — Michele L. Lawson; Smith & Hopen, P.A.

(57) ABSTRACT

A method of treating psychosis, and the underlying antipsychotic formulation. The method includes administering a therapeutically effective amount of synthetic agents that selectively recruit β-arrestin to D2 receptors and have little-to-no binding to culprit receptors associated with weight gain and Type II diabetes. The synthetic agents can include SYA16263 and SYA16264, and/or derivatives or analogs thereof. The 1-(pyridin-2-yl)piperazine moiety was found to play a significant role in recruiting β-arrestin to D2 receptors. In other embodiments, the current invention relates to synthetic agents that are selective of D4 receptors for treatment of psychosis and erectile dysfunction. The synthetic agents can include SYA27287 and/or derivatives or analogs thereof. In all embodiments, extrapyramidal side effects are eliminated or minimized.

2 Claims, 16 Drawing Sheets

(56) References Cited

OTHER PUBLICATIONS

Reeve et al., Simple Device for Quantifying Drug Effects on the Righting Reflex. Pharmacol Biochem Behav. 1992. vol. 42: 183-185.
Sampson et al., Identification of a New Selective Dopamine D4 Receptor Ligand. Bioorg Med Chem. 2014. vol. 22: 3105-3114.
Shimokawa et al., High performance liquid chromatographic methods for the determination of aripiprazole with ultraviolet detection in rat plasma and brain: Application to the pharmacokinetic study. J Chromatogr B. 2005. vol. 821: 8-14.
Sikazwe et al., Haloperidol: towards further understanding of the structural contributions of its pharmacophoric elements at D2-like receptors. Bioorg Med Chem Lett. 2004. vol. 14: 5739-5742.
Addy et al., Reversal of Clozapine Effects on Working Memory in Rats with Fimbria-Fornix Lesions. Neuropsychopharmacology. 2005. vol. 30: 1121-1127.
Hadley. D4 Receptors and Their Antagonists. Medicinal Research Reviews. 1996. vol. 16 (No. 6): 507-526.
Masri et al., Antagonism of dopamine D2 receptor/beta-arrestin 2 interaction is a common property of clinically affective antipsychotics. PNAS.2008. vol. 105 (No. 36): 13656-13661.
International Search Report and Written Opinion for PCT/US18/17600 (filing date: Feb. 9, 2018) dated Apr. 20, 2018; Applicant: Florida A&M University.
International Preliminary Report on Patentability for PCT/US2018/017600 (filing date: Feb. 9, 2018) dated Mar. 25, 2019; Applicant: Florida A&M University.

* cited by examiner

SYA 16263 [CLog P = 4.36]

Haloperidol [CLog P = 3.85]

X = 4F; SYA23012 [CLog P = 5.10]
X = 3F; SYA23013 [CLog P = 5.10]

SYA 27287

IDENTIFICATION OF AGENTS DISPLAYING FUNCTIONAL ACTIVATION OF DOPAMINE D2 AND D4 RECEPTORS

CROSS-REFERENCE TO RELATED APPLICATIONS

This nonprovisional application is a continuation of and claims priority to PCT/US 18/17600, entitled "Identification of Agents Displaying Functional Activation of Dopamine D2 and D4 Receptors", filed Feb. 9, 2018, and to U.S. Provisional Patent Application No. 62/457,491, entitled "Identification of Agents Displaying Functional Selectivity at the Dopamine D2 Receptor", filed Feb. 10, 2017, and to U.S. Provisional Patent Application No. 62/471,624, entitled "Identification of Agents Displaying Functional Selectivity at the Dopamine D2 and D4 Receptors", filed Mar. 15, 2017, both by the same inventors, the contents of which are all hereby incorporated by reference into this disclosure.

FEDERALLY SPONSORED RESEARCH OR DEVELOPMENT

This invention was made with Government support under Grant No. GM 088451 awarded by the National Institutes of Health. The government has certain rights in the invention.

BACKGROUND OF THE INVENTION

1. Field of the Invention

This invention relates, generally, to psychosis and other mental illnesses. More specifically, it relates to the treatment of psychosis and in particular schizophrenia.

2. Brief Description of the Prior Art

Current drugs for treating psychosis and in particular schizophrenia suffer from significant side effects including extrapyramidal side effects, weight gain and Type-II diabetes. Attempts, however unsuccessful, have been made to overcome these drawbacks, for example including U.S. Patent Application Publication No. 2002/0103105, which is incorporated herein by reference.

Accordingly, what is needed is an antipsychotic that eliminates or at least minimizes the damaging side effects. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved antipsychotic or erectile dysfunction treatment is now met by a new, useful, and nonobvious invention.

In an embodiment, the current invention is a method of treating psychosis (e.g., schizophrenia) in a subject, comprising the step of administering a therapeutically effective amount of a synthetic agent (e.g., SYA16263, SYA16264, and analogs/derivatives thereof) in a pharmaceutically effective carrier. The synthetic agent selectively recruits $\beta$-arrestin to D2 dopamine receptors, such that the subject is substantially free of extrapyramidal symptoms upon administration of the synthetic agent. If the synthetic agent used is SYA16263 or analog thereof, the therapeutically effect amount administered may be about 1 mg/kg of the subject, or more specifically at least about 50 mg/kg of the subject. If the synthetic agent used is SYA16264 or analog thereof, the therapeutically effective amount administered may be about 1 mg/kg of the subject. In alternative embodiments, the synthetic agent includes a 1-(pyridin-2-yl)piperazine or a 2-(piperazin-1-yl)pyrimidine moiety.

In a separate embodiment, the current invention is a method of reversing cognitive deficits associated with psychosis, comprising the step of administering a therapeutically effective amount of a synthetic agent in a pharmaceutically effective carrier. The synthetic agent is selective for D4 dopamine receptors, such that the subject is substantially free of extrapyramidal symptoms upon administration of the synthetic agent. The synthetic agent may be SYA27287 (and/or analogs/derivatives thereof), and in this case, the therapeutically effective amount administered can be at least about 1 mg/kg of the subject.

In a separate embodiment, the current invention is a method of treating erectile dysfunction, comprising the step of administering a therapeutically effective amount of a synthetic agent in a pharmaceutically effective carrier, where the synthetic agent is selective of D4 dopamine receptors. The synthetic agent may be SYA27287 (and/or analogs/derivatives thereof), and in this case, the therapeutically effective amount administered can be at least about 1 mg/kg of the subject.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
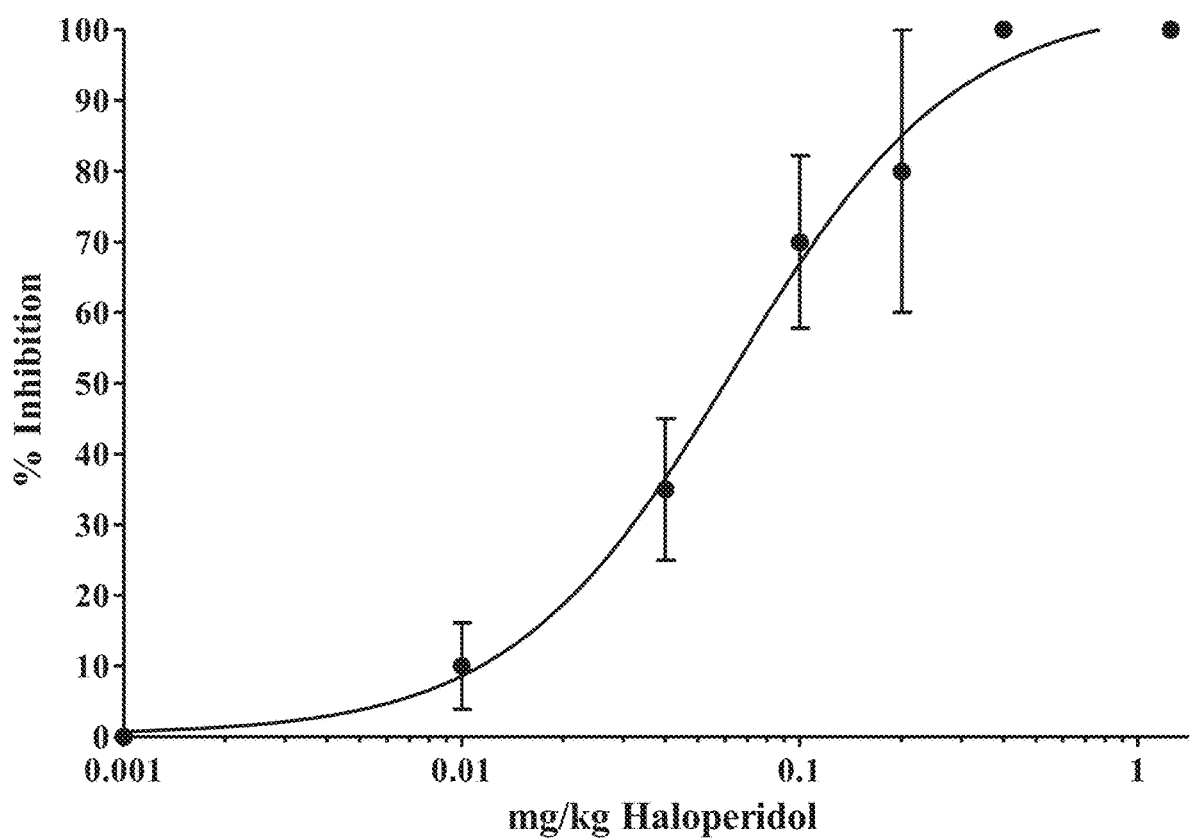
FIG. 1 shows that haloperidol inhibited apomorphine (APO)-induced climbing behavior in mice with an $ED_{50}$ of 0.169 μmole/kg (0.064 mg/kg), n=5 mice/dose. Error bars are SEM.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

As used herein, "about" means approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'".

As used herein, "treat", "treatment", "treating", and the like refer to acting upon a condition (e.g., psychosis, schizophrenia, erectile dysfunction or symptom thereof) with an agent to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., regression of mental illness).

As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

The term "therapeutically effective amount" as used herein describes concentrations or amounts of components such as agents which are effective for producing an intended result, including psychosis treatment. Compositions according to the present invention may be used to affect a favorable change in the illness, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

The term "administration" or "administering" is used throughout the specification to describe the process by which a composition comprising the agents discussed herein, is delivered to a patient or individual for therapeutic purposes. The composition of the subject invention and methodology in use thereof can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments.

Administration will often depend upon the amount of compound administered, the number of doses, and duration of treatment. In an embodiment, multiple doses of the agent are administered. The frequency of administration of the agent can vary depending on any of a variety of factors, such as level of psychosis, and the like. The duration of administration of the agent, e.g., the period of time over which the agent is administered, can vary, depending on any of a variety of factors, including patient response, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted.

As used herein, the term "subject," "patient," or "organism" includes humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

As used herein, the term "psychosis" refers to a mental disorder—from early onset to late stage—in which a subject or patient's thoughts, emotions, or other mental capacities lose contact with external reality. The individual may exhibit personality changes, unusual behavior, difficulties in social interactions, and/or difficulties in daily activities. Examples of psychosis can include a range of conditions, from milder aberrant experiences to severe schizophrenia and bipolar disorder.

As used herein, the term "extrapyrimidal symptoms" refers to physical side effects experienced by an individual who has been administered conventional antipsychotic medications. These side effects relate to the individual's posture and skeletal muscle tone, and include, but are not limited to, tremor, slurred speech, akathesia, acute dyskinesias and dystonic reactions, tardive dyskinesia, anxiety, distress, paranoia, bradyphrenia, Parkinsonism, akinesia, akathisia, and neuroleptic malignant syndrome. Conventional antipsychotic medications typically lead to one or more extrapyramidal symptoms by blockading or depleting dopamine in the basal ganglia; this reduction or lack of dopamine often mimics idiopathic pathologies of the extrapyramidal system.

D2 Receptors

In certain embodiments, the current invention includes functionally selective agents that recruit $\beta$-arrestin to the D2 receptor in order to produce a therapeutic effect but without the Parkinsonism-like side effects (e.g., extrapyramidal side effects, weight gain and Type-II diabetes) associated with conventional antipsychotic agents. In other embodiments, the current invention is a therapy for psychosis and/or schizophrenia utilizing said functionally selective agents, such that the unwanted Parkinsonism-like side effects are not experienced by the user/patient.

Additionally, it has been reported that conventional agents that bind significantly to the serotonin 5-HT2C and histamine H1 receptors and act as antagonists are associated with weight gain observed in several second-generation antipsychotic drugs. Utilizing methodologies and formulations of the current invention, synthetic agents were identified to selectively recruit $\beta$-arrestin to the D2 receptor and have little-to-no binding to culprit receptors associated with weight gain, Type II diabetes, and extrapyramidal symptoms, such that the patient/subject is substantially free of these symptoms/side effects upon being administered the agent.

As used herein, the term "little-to-no binding" refers to a particular agent not having a capability of ligating to a particular receptor, or at the minimum, an amount of the agent that does ligate to the receptor is not sufficient to produce a negative physiological effect (e.g., weight gain Type II diabetes, extrapyramidal symptoms). In other words, the individual being administered the agent is substantially free of said negative physiological effect. As used herein, the term "substantially free" refers to a patient or subject being administered one or more of the agents discussed herein not experiencing the harmful symptoms that are side effects of conventional antipsychotic medications. Alternatively, and at the very least, the patient or subject would experience significantly less of the harmful symptoms that are side effects of conventional antipsychotic medications.

In addition to their utility for the treatment of schizophrenia, the new agents may serve as standard agents to probe the effect of functional selectivity in drug development.

EXAMPLE 1

Evaluation of SYA16263

A. Animals

Reversal of apomorphine (APO)-induced climbing behavior experiments were performed using male, albino, Swiss-Webster mice (21-29 g; 5-7 weeks old) to predict potential antipsychotic activity. Catalepsy experiments were carried out on male Sprague-Dawley rats (107-168 g), (5-6 weeks old). All animals were from HARLAN Laboratories, Inc. Animals were housed in the Florida A&M University Animal Care facility which is fully AAALAC-accredited and operates with a 12 h light/dark cycle and controlled temperature (24±2° C.). Animals were given free access to food and water and at least 5 days to adjust before experiments were begun. Animals were fasted the night before each experiment. All experimental procedures were performed in accordance with protocols approved by Florida A&M University Institutional Animal Care and Use Committee.

B. Drugs and Chemicals

SYA16263 (Clog P=4.36) was synthesized at Florida A&M University with CHN values within 0.4% of theoretical values as determined by CHN analysis. The free bases were dissolved in filtered (0.22µ) 1% lactic acid vehicle for all animal studies.

Haloperidol and apomorphine hydrochloride hemihydrate were obtained from SIGMA ALDRICH. Haloperidol was dissolved in filtered (0.22µ) 1% lactic acid. APO was dissolved in HPLC grade water, followed by ascorbic acid (0.1% w/w) dissolution and followed by NaCl (0.9% w/w) the morning of the experiments in an amber vial and 1.5 mg/kg apomorphine (as free base) injected. Ascorbic acid and lactic acid were ACS reagent grade (ACROS); phosphate buffered saline (PBS) and NaCl were from FISHER, ACS grade; and the $H_2O$ used to make solutions was HPLC grade. Diethyl ether was obtained from FLUKA, residue analysis grade. The acetic acid, $H_2O$, methanol, and acetonitrile were HPLC grade. The sodium sulfate was analytical reagent grade.

Doses are expressed as the free base for all compounds and were administered in a volume of 10 mL/kg by intraperitoneal (ip) injection, except for APO which was administered by subcutaneous (sc) injection.

The HPLC internal standard, DS-49, used for calibration was synthesized at Florida A&M University (Sikazwe D M N, Li S, Mardenborough L, Cody V, Roth B L, Ablordeppey S Y. Haloperidol: towards further understanding of the structural contributions of its pharmacophoric elements at D2-like receptors. Bioorg Med Chem Lett 2004; 14:5739-42) with CHN values within 0.4% of theoretical values as determined by CHN analysis.

The reported Clog P values were calculated using CHEMDRAW ULTRA, version 11.0.1 obtained from CAMBRIDGESOFT.

C. Behavioral Experiments and Results

All statistical analyses were performed using PRISM 5.03, GRAPHPAD Software Inc. Pharmacokinetic parameters were calculated by non-compartmental analysis using PK SOLUTIONS, Summit Research Services. All error bars are standard error of the mean (SEM).

i. Reversal of Apomorphine-Induced Climbing

A modified climbing test (Needham P L, Atkinson J, Skill M J, Heal D J. Zotepine: Preclinical Tests Predict Antipsychotic Efficacy and an Atypical Profile. Psychopharmacol Bull 1996; 32:123-8; Protais, P, Costentin, J, Schwartz J C. Climbing Behavior Induced by Apomorphine in Mice: a Simple Test for the Study of Dopamine Receptors in Striatum. Psychopharmacology 1976; 50:1-6) was used with Swiss-Webster mice to predict potential antipsychotic activity. Inhibition or reduction of apomorphine-induced climbing was deemed indicative of antipsychotic properties. Five mice per dose were injected first with haloperidol (brand name HALDOL), SYA16263, or vehicle, and then returned to their home cage. Thirty minutes later, the mice were injected with 1.5 mg/kg (as free base) apomorphine and placed in cylindrical wire cages (12 cm diameter, 14 cm height).

Climbing behavior was observed at 10 and 20 minutes after the apomorphine injection. Climbing behavior was assessed as follows. A score of 2 (0% inhibition) was assigned if all 4 paws were observed to be on the cage wall and not on the floor. A score of 1 (partial inhibition) was assigned if 3 or 2 paws were observed to be on the cage wall. A score of 0 (100% inhibition) was assigned if 1 or 0 paws were observed to be on the cage wall.

Figure 2:
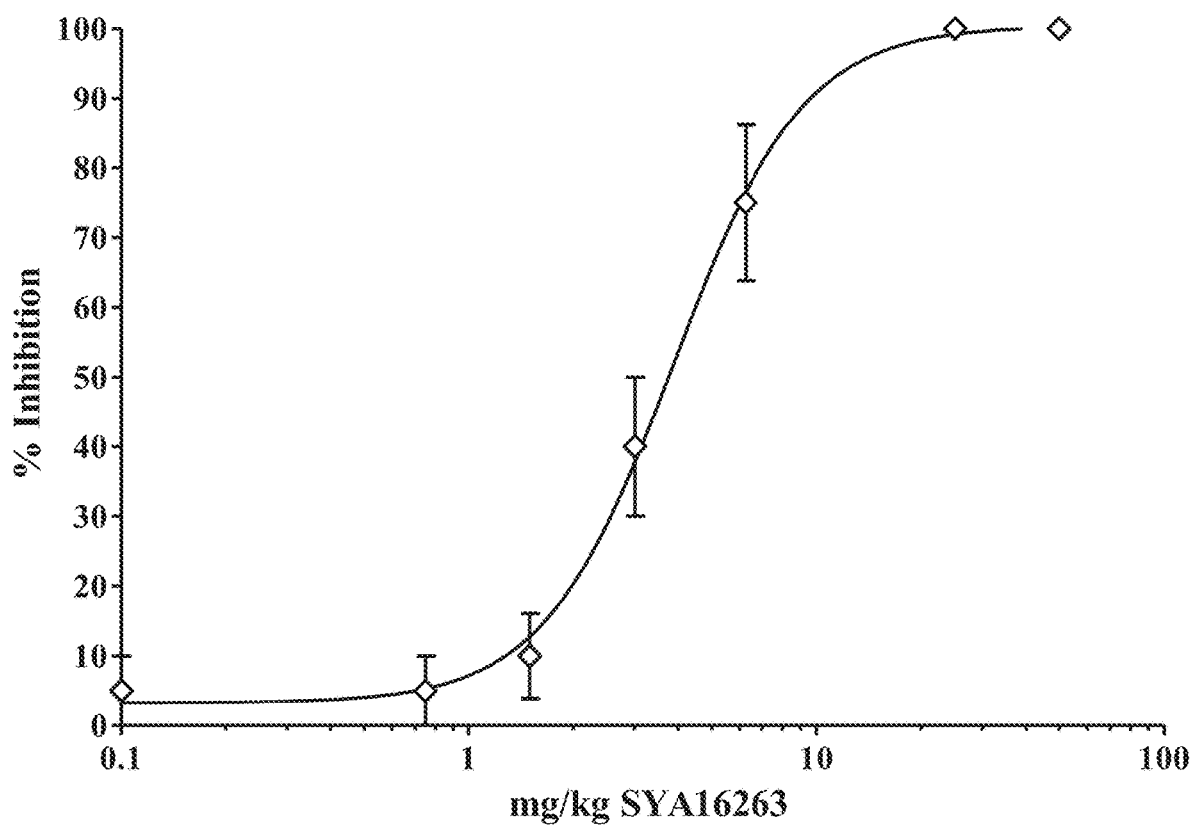
FIG. 2 shows that SYA16263 inhibited APO-induced climbing behavior in mice with an ip $ED_{50}$ of 12.4 μmole/kg (3.88 mg/kg), n=5 mice/dose. Error bars are SEM.

Scores were expressed as mean percent climbing inhibition and can be seen in FIGS. 1-2. PRISM 5.03, GRAPHPAD Software, Inc., non-linear regression software was used to calculate $ED_{50}$s. Both haloperidol and SYA16263 caused inhibition of climbing, with nearly 100% of mice exhibiting inhibition of climbing at higher dosages of each agent. More specifically, haloperidol reversed APO-induced climbing behavior in mice in a dose dependent manner as shown in FIG. 1, with an ip $ED_{50}$ of 0.17 µmole/kg (0.064 mg/kg). SYA16263 reversed APO-induced climbing behavior in mice in a dose-dependent manner (FIG. 2) with an ip $ED_{50}$ of 12.4 µmole/kg (3.88 mg/kg). This efficacy indicates that SYA16263 may serve as an antipsychotic agent.

ii. Catalepsy Assessment

To assess the potential for extrapyramidal side effects (EPS) in humans, the catalepsy bar test was used with rats (Kleven M S, Barret-Grevoz, C, Slot, L B, Newman-Tancredi, A. Novel antipsychotic agents with $5-HT_{1A}$ agonist properties: Role of $5-HT_{1A}$ receptor activation in attenuation of catalepsy induction in rats. Neuropharmacology 2005; 49:135-43; Hoffman D C, Donovan H. Catalepsy as a rodent model for detecting antipsychotic drugs with extrapyramidal side effect liability. Psychopharmacology 1995; 120:128-33); utilizing a semi-automated instrument from MED ASSOCIATES, Inc., St. Albans, Vt. (Bricker B, Jackson T, Boateng B, Zhu X Y, Ablordeppey S Y. Evaluation of the behavioral and pharmacokinetic profile of SYA013, a homopiperazine analog of haloperidol in rats. Pharm Biochem Beh 2012; 102:294-301). In addition, following the methods of Depoortere et al., 2007 (Depoortere R, Bardin L, Auclair A L, Kleven M S, Prinssen E, Colpaert F, Vacher B, Newman-Tancredi A. F15063, a compound with $D_2/D_3$ antagonist, $5-HT_{1A}$ agonist and $D_4$ partial agonist properties: (II) Activity in models of positive symptoms of schizophrenia. Br J Pharmacol 2007; 151:253-65) and Kleven et al., 2005, the crossed-legs position (CLP) test was used, which is a second test of catalepsy that is known to be sensitive to the anticataleptic actions of $5HT_{1A}$ receptor agonists.

Following the two catalepsy tests, a righting test (McCreary A C, Glennon J C, Ashby C R Jr, Meltzer H Y, Li Z, Reinders J H, Hesselink M B, Long S K, Herremans A H, Stuivenberg H V Feenstra R W, Kruse C G. SLV313 (1-(2,3-DihydroBenzo[1,4]-Dioxin-5-yl)-4-[5-(4-Fluoro-Phenyl)-Pyridin-3-ylmethyl]-PiperazineMonohydrochloride): A Novel Dopamine $D_2$ Receptor Antagonist and $5-HT_{1A}$ Receptor Agonist Potential Antipsychotic Drug. Neuropsychopharmacology 2007; 32:78-94; Reeve B, Dingwall B, Darlington C L, Scott S J, Sansom A J, Smith P F. Simple Device for Quantifying Drug Effects on the Righting Reflex. Pharmacol Biochem Behav 1992; 42:183-85) was performed to check for sedation or other effects.

Rats were injected ip, and then 60 minutes later, the rats were tested in the CLP test for 30 s. This was followed by the bar test for 30 s and then the righting test. The rats were then returned to their home cage. This was repeated at 3 min and 6 min from the start of the first trial. Five rats were used for each dose. The mean of the 3 trials was used as the catalepsy response for each test for each rat (Depoortere et al., 2007; Kleven et al., 2005).

iii. Catalepsy Crossed-Legs Position (CLP) Test

Rats were placed on the stainless-steel floor of the catalepsy test chamber. Each rat's abdomen pointed towards the floor, with the hind paws brought forward and the front paws backward so that the ipsilateral hind paws could hold onto the top of the front paws. The time (measured with a stopwatch) that each rat stayed in this position with either one or both sets of paws was recorded up to 30 s (Depoortere et al., 2007; Kleven et al., 2005).

Figure 3:
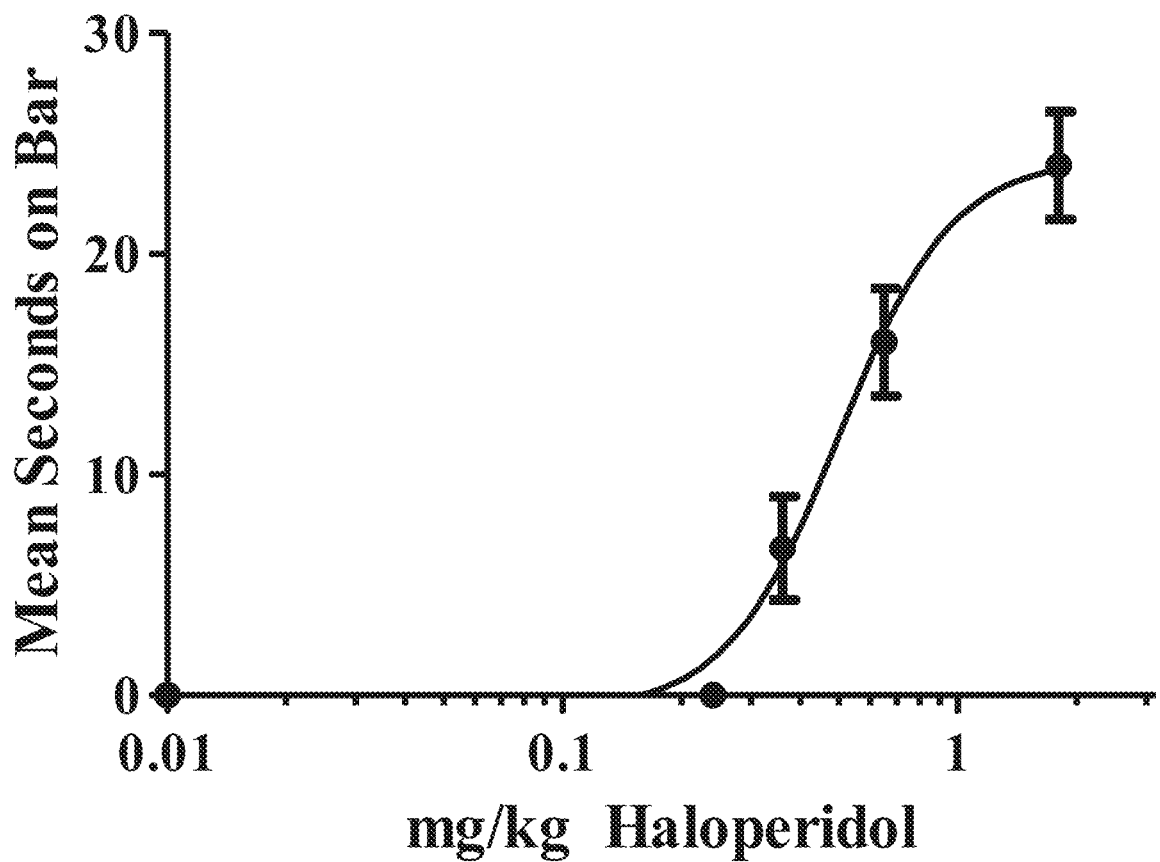
FIG. 3 shows that haloperidol demonstrated significant catalepsy with large effect in rats in the CLP test, with an ip $AED_{50}$=1.3 μmole/kg (0.50 mg/kg) in the CLP test. n=5-9 rats/dose. Error bars are SEM.

As seen in FIG. 3, haloperidol displayed significant CLP catalepsy in a dose dependent manner, with catalepsy $AED_{50}s$ (adverse effect dose) of 1.3 μmole/kg (0.50 mg/kg).

iv. Catalepsy Bar Test

Forelimbs of each rat were placed on a 1.3 cm-diameter horizontal metal bar at 10-cm height in an individual catalepsy chamber. Contact time with both the bar and the floor was measured up to 30 seconds by the instrument for each chamber, with the use of a stopwatch as backup if required. Four chambers were used (Depoortere et al., 2007; Kleven et al., 2005).

Figure 4A:
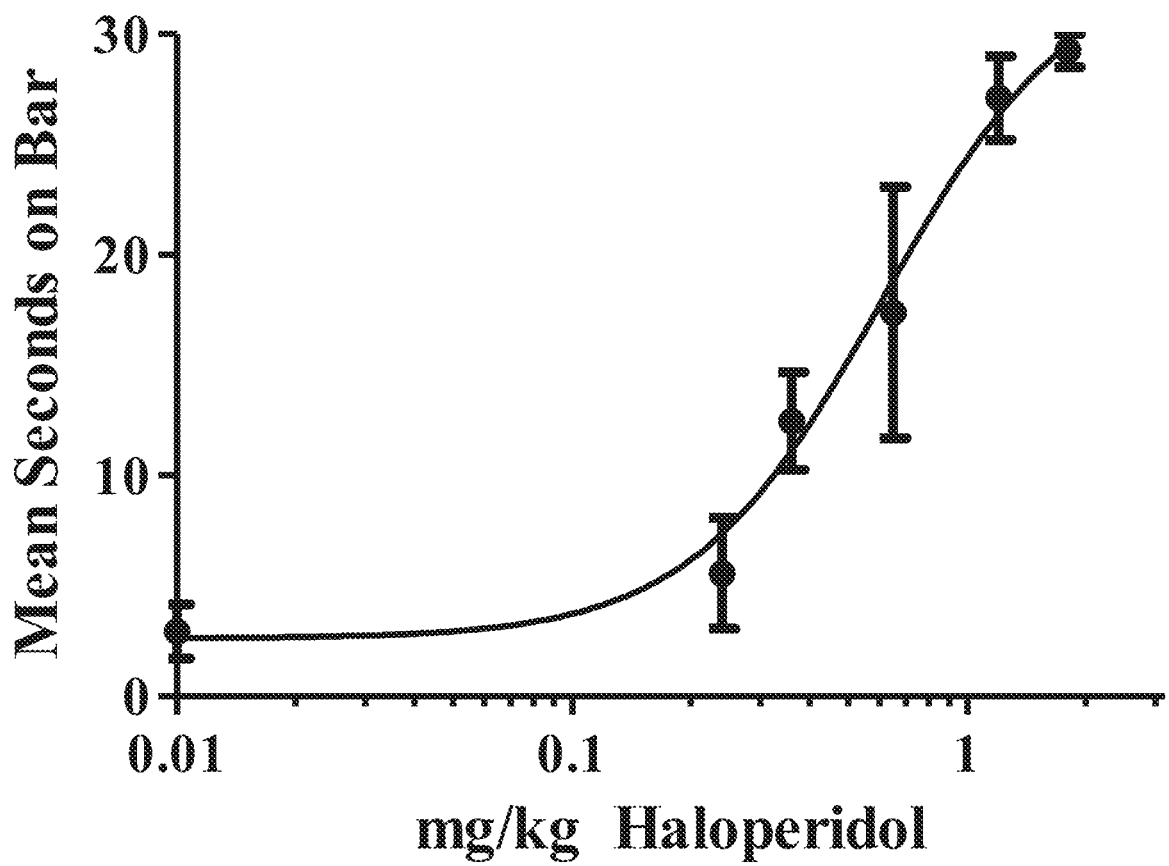
FIG. 4A shows that haloperidol demonstrated significant catalepsy with large effect in rats in the bar test, with an ip $AED_{50}$=1.6 μmole/kg (0.61 mg/kg) in the bar test. n=5-9 rats/dose. Error bars are SEM.
Figure 4B:
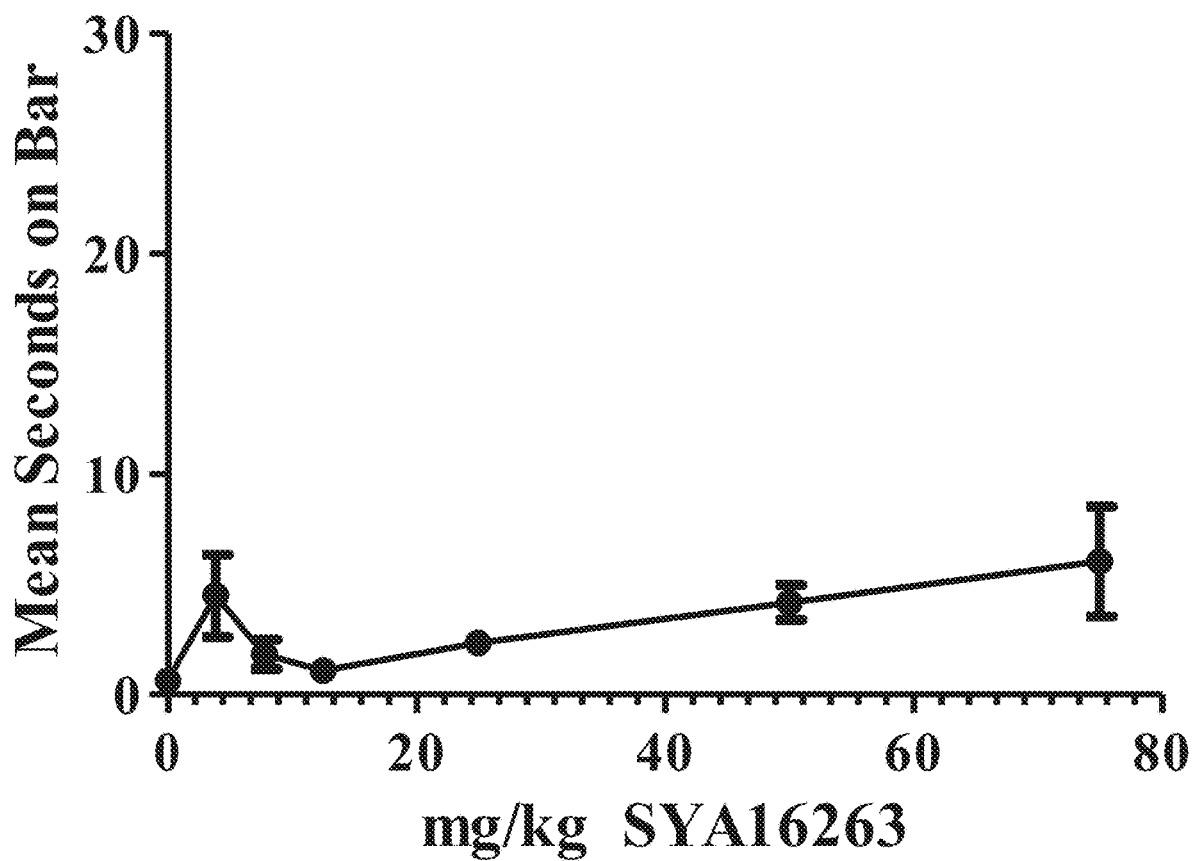
FIG. 4B shows that no bar catalepsy (mean <20 seconds on bar) was observed for up to 239 μmole/kg (75 mg/kg) SYA16263 (19×$ED_{50apom}$) n=5 rats/dose. Error bars are SEM.

As seen in FIG. 4A, haloperidol displayed significant bar catalepsy in a dose dependent manner, with catalepsy $AED_{50}s$ (adverse effect dose) of 1.6 μmole/kg (0.61 mg/kg). As seen in FIG. 4B, SYA16263 displayed no catalepsy (mean time on bar <20 seconds) up to $19 \times ED_{50apom}$ (239 μmole/kg or 75 mg/kg). Catalepsy $AED_{50}$ was found to be >75 mg/kg. No catalepsy was detected with the CLP test with 0 s response for all doses up to 75 mg/kg.

v. Righting Test

Rats were placed on their backs and observed immediately following the CLP and bar tests. If the rat did not stay in this position, and flipped over without assistance, it was scored as "righted" (McCreary et al., 2007; Reeve et al., 1992). All rats were observed to right themselves following CLP catalepsy testing, and all rats were observed to right themselves following bar catalepsy testing of the 75 mg/kg dose.

D. Pharmacokinetic Data for SYA16263, ip, 50 mg/kg Dose, Rats i. Sample Preparation for HPLC-PDA Plasma. 0.5 mL of rat plasma was mixed with 20 μL of DS-49 internal standard (250 μg/mL) in an 8-mL glass vial with a TEFLON-lined cap. 100 μL of 2M NaOH was added and mixed, followed by diethyl ether (5 mL). The tubes were shaken for 10 min. The sample was then centrifuged for 10 min at 3000 rpm. The ether layer was transferred to a 5-mL glass vial and the ether evaporated under nitrogen at 40° C. until dryness. The sample was then reconstituted in 200 μL of mobile phase. The supernatant was transferred to a 0.6 mL high speed plastic centrifuge tube and centrifuged at 10,000 g for 5 min. 100 μL of supernatant was injected for HPLC analysis.

Brain tissue. Rat brains were frozen at −20° C. until needed. Each brain was weighed, and then macerated with a spatula, followed by the addition of 2 parts PBS and homogenization with a TISSUE TEAROR at a maximum speed setting of 30 for 2 min. This was followed by sonification for 20 seconds (3 times) with mixing in between using a BRANSON digital sonifier (model 450), with a microtip, set at 50% amplitude. Homogenates were kept on ice between steps. One mL of homogenate (~1 g) was mixed with 20 μL of 250 μg/mL DS-49 (internal standard, Clog P=5.17) in a 5-mL glass vial with a TEFLON-lined cap. This was mixed with 3 mL of acetonitrile and shaken for 5 min. After centrifugation at 3000 rpm for 10 min, the supernatant was transferred to an 8-mL glass vial with a TEFLON-lined cap and evaporated under $N_2$ at 40° C. until near dryness. This was mixed with 0.5 mL, $H_2O$ and 100 μL 2M NaOH, followed by extraction into 5 mL of ether. Additional cleanup and analysis were performed as described for the plasma samples (Shimokawa Y, Akiyama H, Kashiyama E, Koga T, Miyamoto E. High performance liquid chromatographic methods for the determination of aripiprazole with ultraviolet detection in rat plasma and brain: Application to the pharmacokinetic study. J Chromatogr B 2005; 821:8-14).

HPLC conditions. A WATERS 2695 ALLIANCE HPLC system, equipped with an autosampler and PDA detector, was used. The column was an ALLTIMA HP, C18. 5μ, 4.6 mm×150 mm, protected by a guard cartridge with the same packing, which was changed when peak shape eventually degraded, restoring peak shape back to normal. The flowrate was 1 mL/min, and an analytical wavelength of 254 nm was used. The isocratic mobile phase was generated from 55% A and 45% C; 100% methanol was in the A reservoir; and an aqueous solution of 0.01M sodium sulfate in 4% v/v acetic acid was in the C reservoir. Run time was 15 min. Retention time and PDA spectra were used to identify analytes.

Figure 5:
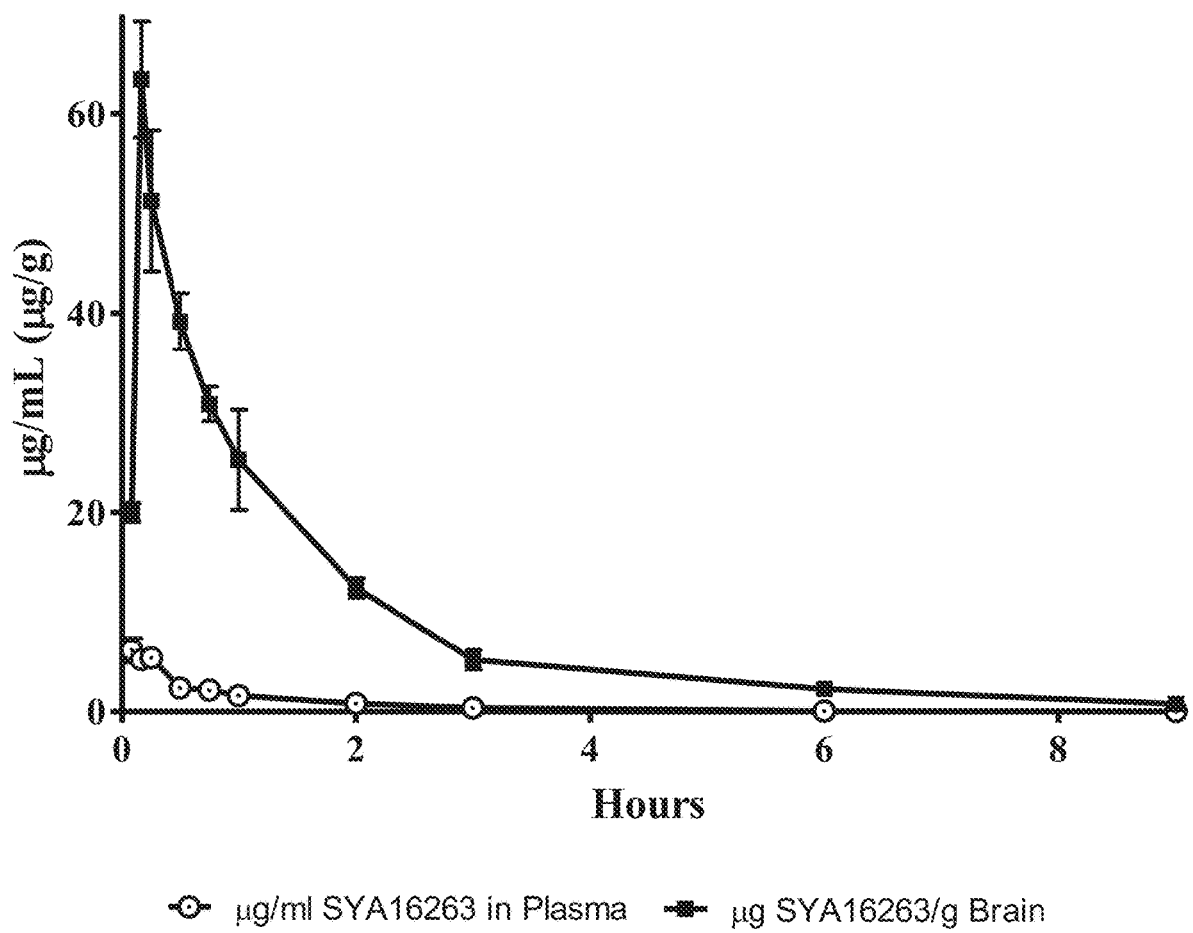
FIG. 5 depicts time profile of plasma and brain concentrations of SYA16263 after ip injection of 50.0 mg/kg SYA16263. Data through 9-hour time point shown for clarity. Although 24-hour point was collected and analyzed, the plasma concentration was below the detection limit, and the brain concentration was also near or below the detection limit.

SYA16263 levels in plasma and brain samples. A single bolus dose of 50 mg/kg SYA16263 ($12.9 \times ED_{50}$) was given by ip injection to an average of 4 rats per time point group. Blood and brains were collected at 5 min, 10 min, 15 min, 30 min, 1 hr, 2 hr, 3 hr, 6 hr, 9 hr, and 24 hr. For control purposes, vehicle was injected into 4 rats as well. Plasma and whole brains were stored at −20° C. until needed. The internal standard method was used to correct for % recoveries. Calibration lines were calculated using linear regression from 7-8 points and had coefficients of determination of 0.9988 or better. A graph of the plasma and brain data for SYA16263 is shown in FIG. 5. Pharmacokinetic parameters are presented in Table 1.

TABLE 1

Pharmacokinetic Data for SYA16263.

| Tissue | Dose, mg/kg | $C_{max\ obsvd}$ μg/g | $T_{max\ obsvd}$, h | $AUC_{0-t}$ μg · h/ (mL or g) | $t_{1/2}$, h, elimination |
|---|---|---|---|---|---|
| Brain | 50 | 63.5 | 0.17 | 86 | 2.9-3.1 |
| Plasma | 50 | | | 5.4 | 0.74-0.98 |

In the brain, $t_{max}$ was 10 min, $BB=C_{brain}/C_{plasma}=63.5/5.23=12.1$, and Log BB=1.08. This means the concentration of SYA16263 in the brain was 12 times that in the plasma at the ~equilibrium point. This, and a log BB>0.3 suggests that SYA16263 readily crosses the BBB.

Figure 6:
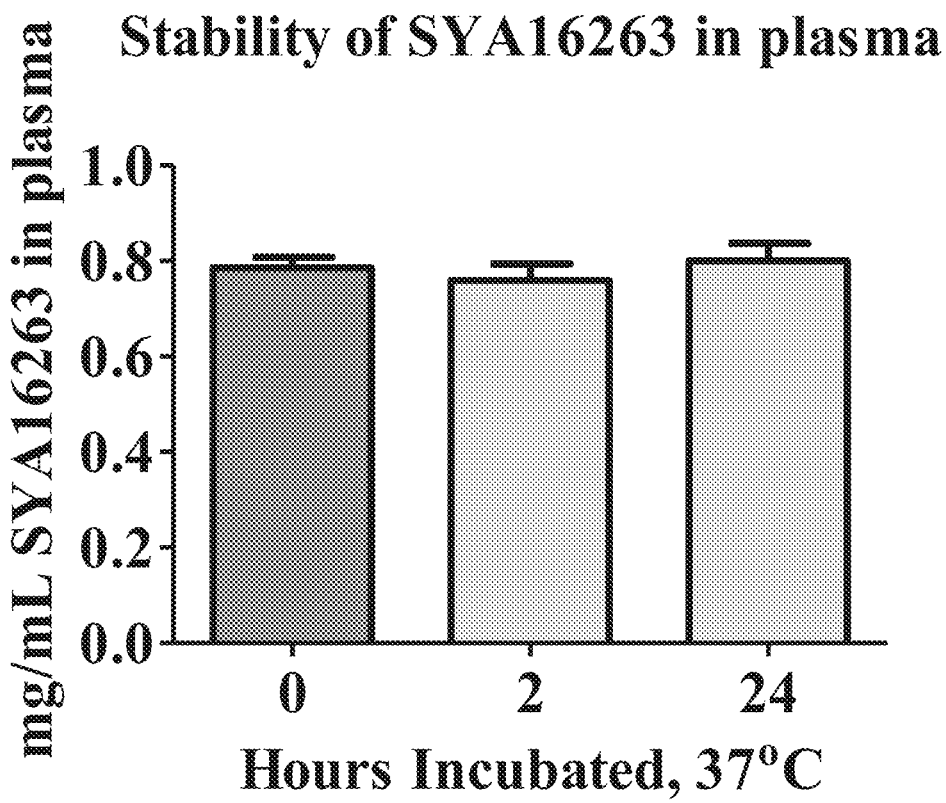
FIG. 6 depicts results of a stability test of SYA16263 in rat plasma.

Stability data. The stability of SYA16263 was investigated in plasma. Stored rat plasma was spiked with SYA16263 in vehicle (1% lactic acid) to give 0.71 mg SYA16263/mL plasma, which is an estimate of the resulting plasma concentration for a 50 mg/kg dose for a rat. Triplicate samples were incubated at 37° C. for 0, 2, and 2.4 hours. After storage in the freezer, sample extraction and cleanup procedures, the extracts were analyzed by HPLC. RSD peak area=2.5%. Results are presented in FIG. 6. As indicated, no loss of SYA16263 was observed over the 24 h period.

EXAMPLE 2

$D_2R$ β-Arrestin Recruitment Tango Assay

Recruitment of β-arrestin to agonist-stimulated $D_2R$ (D2 receptors) was performed using the "Tango"-type assay described in Barnea (Barnea G, Strapps W, Herrada G, Berman Y, Ong J, Kloss B, Axel R, Lee K J. The genetic design of signaling cascades to record receptor activation Proc Natl Acad Sci USA 2008; 105:64-69) to evaluate SYA16263 and SYA16264.

Briefly, HTLA cells (an HEK293-derived cell line containing stable integrations of a tTA-dependent luciferase reporter and a β-arrestin2-TEV fusion gene) stably expressing β-arrestin-TEV protease and a tetracycline transactivator-driven luciferase were plated in 15-cm dishes in DMEM (DULBECCO'S MODIFIED EAGLE MEDIUM, THERMO FISHER) containing 10% FBS and transfected with D2V2-TCS-tTA construct. The next day, the cells were plated, and the following day, they were challenged with the reference agonist (6 μM) or $D_2$ test ligand (6 μM).

After 18 h, the medium was removed and replaced with 1× BRITEGLO reagent (PROMEGA), and each well's luminescence was read using a TRILUX plate reader. Data were normalized to vehicle (0%) and quinpirole (100%) controls and regressed using the sigmoidal dose-response function built into GRAPHPAD PRISM 4.0.0. The results are reported in Table 2.

restin-2 to the $D_2R$ (Table 2); rather, it acts as an antagonist at both the dependent and independent signaling pathways at the $D_2R$ and thus SYA23013 demonstrates catalepsy in rats. These results are also consistent with previous reports by Allen (Allen J A, Yost J M, Setola V, Chen X, Sassano M F, Chen M, Peterson S, Yadav P N, Huang X P, Feng B, Jensen N H, Che X, Bai X, Frye S V, Wetsel W C, Caron M G, Javitch J A, Roth B L, Jin J. Discovery of beta-arrestin-biased dopamine D2 ligands for probing signal transduction pathways essential for antipsychotic efficacy. Proc Natl Acad Sci USA; 2011; 108: 18488-18493), which showed that activation of β-arrestin signaling is associated with antipsychotic action and protects against the induction of catalepsy.

EXAMPLE 3

Comparative Pharmacological Evaluation

Figure 9A:
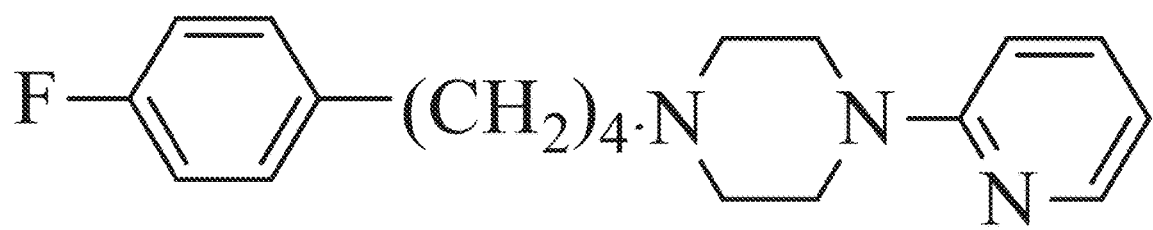
FIG. 9A depicts the structure of SYA16263.
Figure 9B:
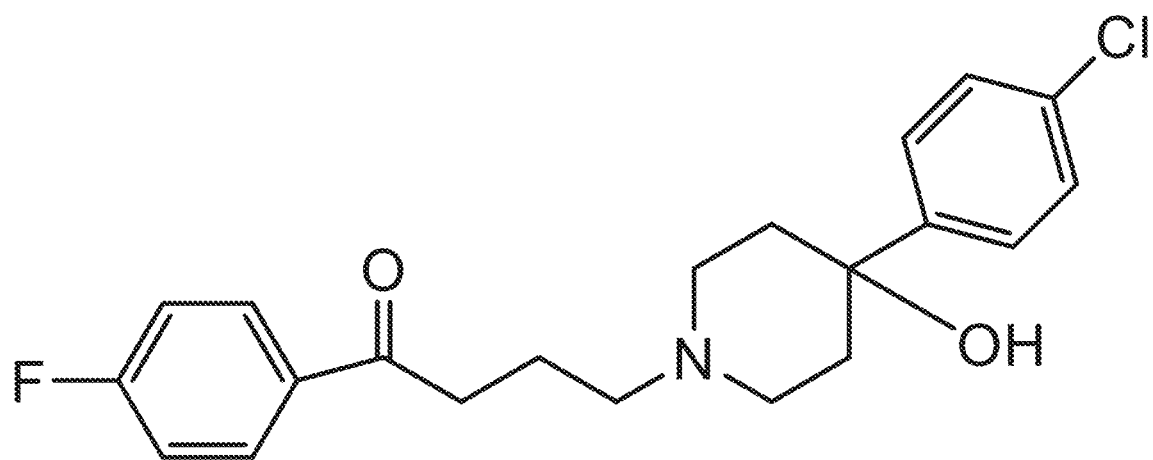
FIG. 9B depicts the structure of haloperidol.
Figure 9C:
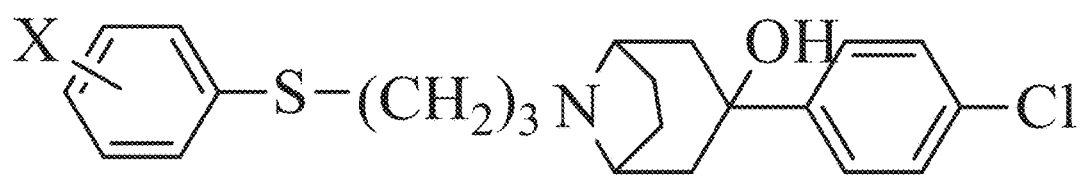
FIG. 9C depicts the structures of SYA23012 and SYA23013.
Figure 10A:
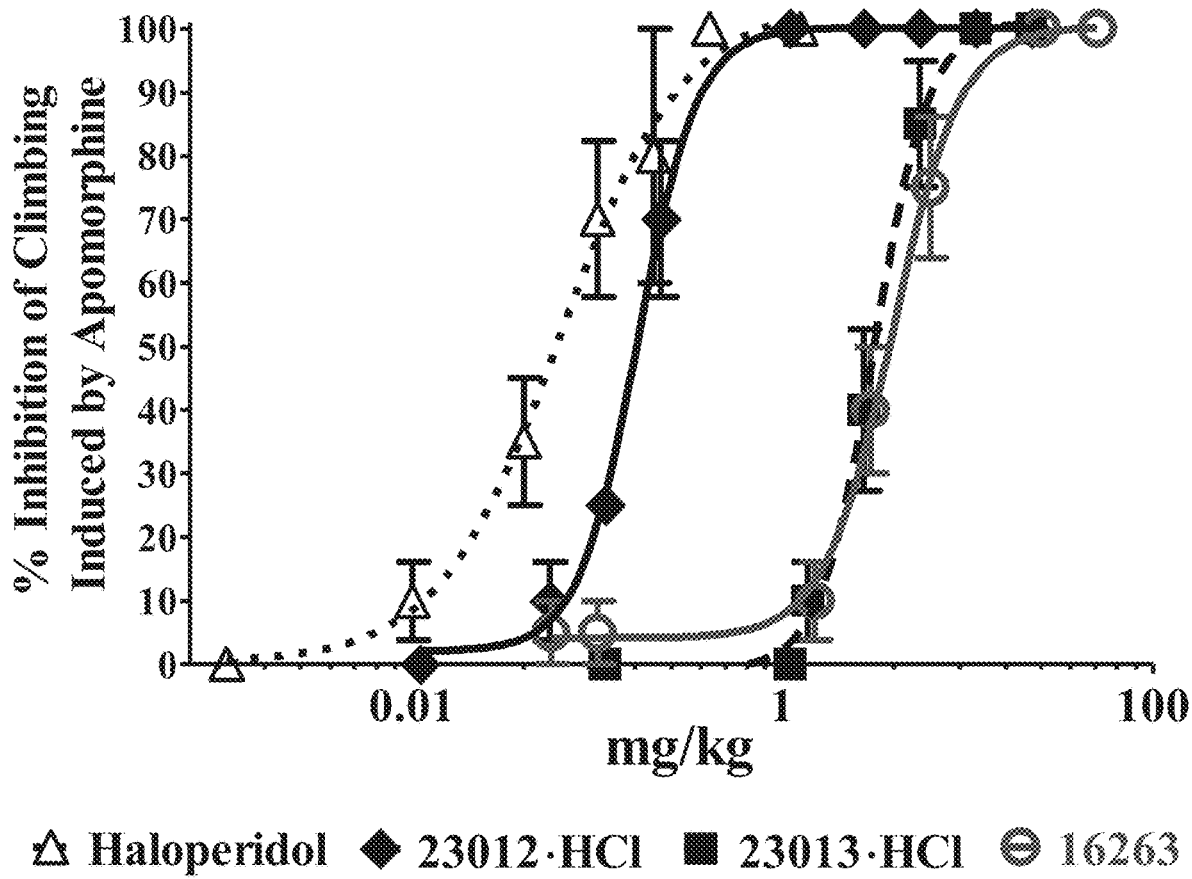
FIG. 10A depicts percentage inhibition of climbing upon administration of haloperidol and tropane analogs, SYA23012, SYA23013, and SYA16263.
Figure 10B:
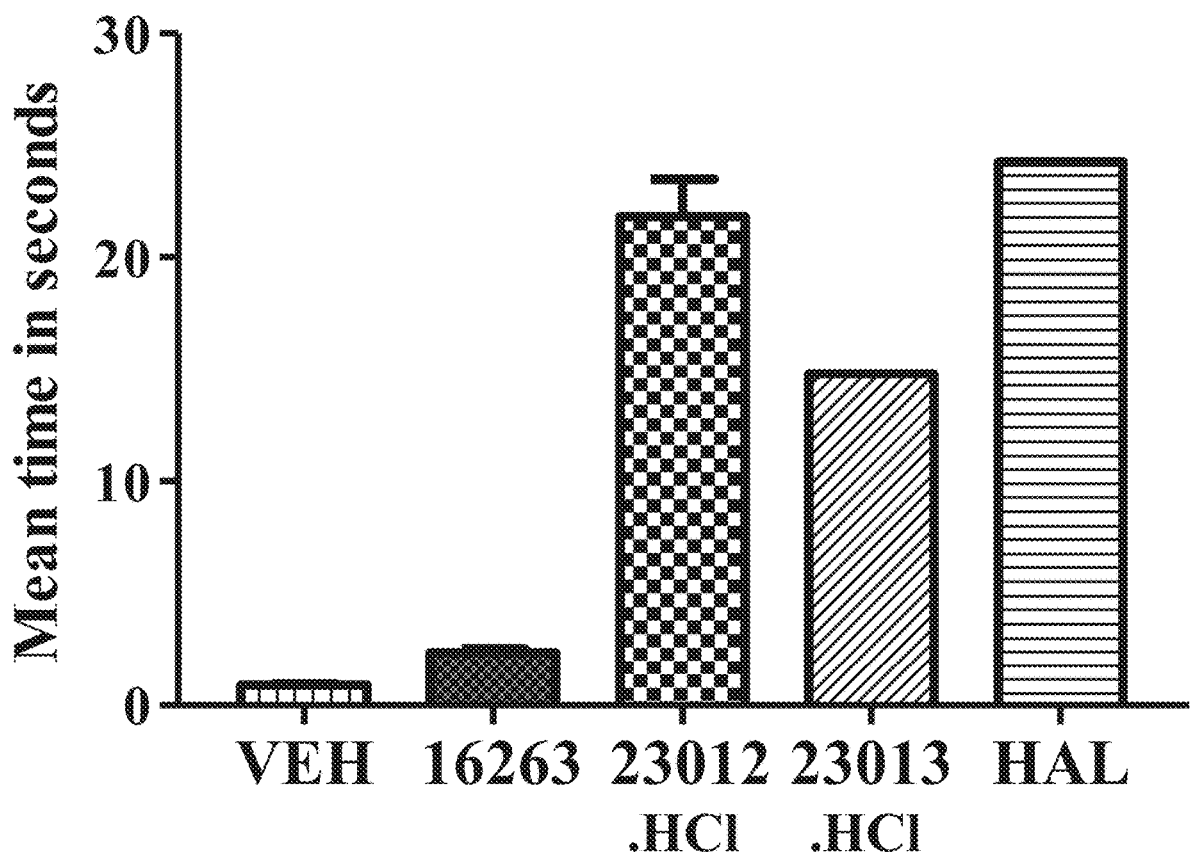
FIG. 10B depicts results of catalepsy bar test upon administration of SYA16263. SYA23012, SYA23013, and haloperidol and tropane analogs.
Figure 10C:
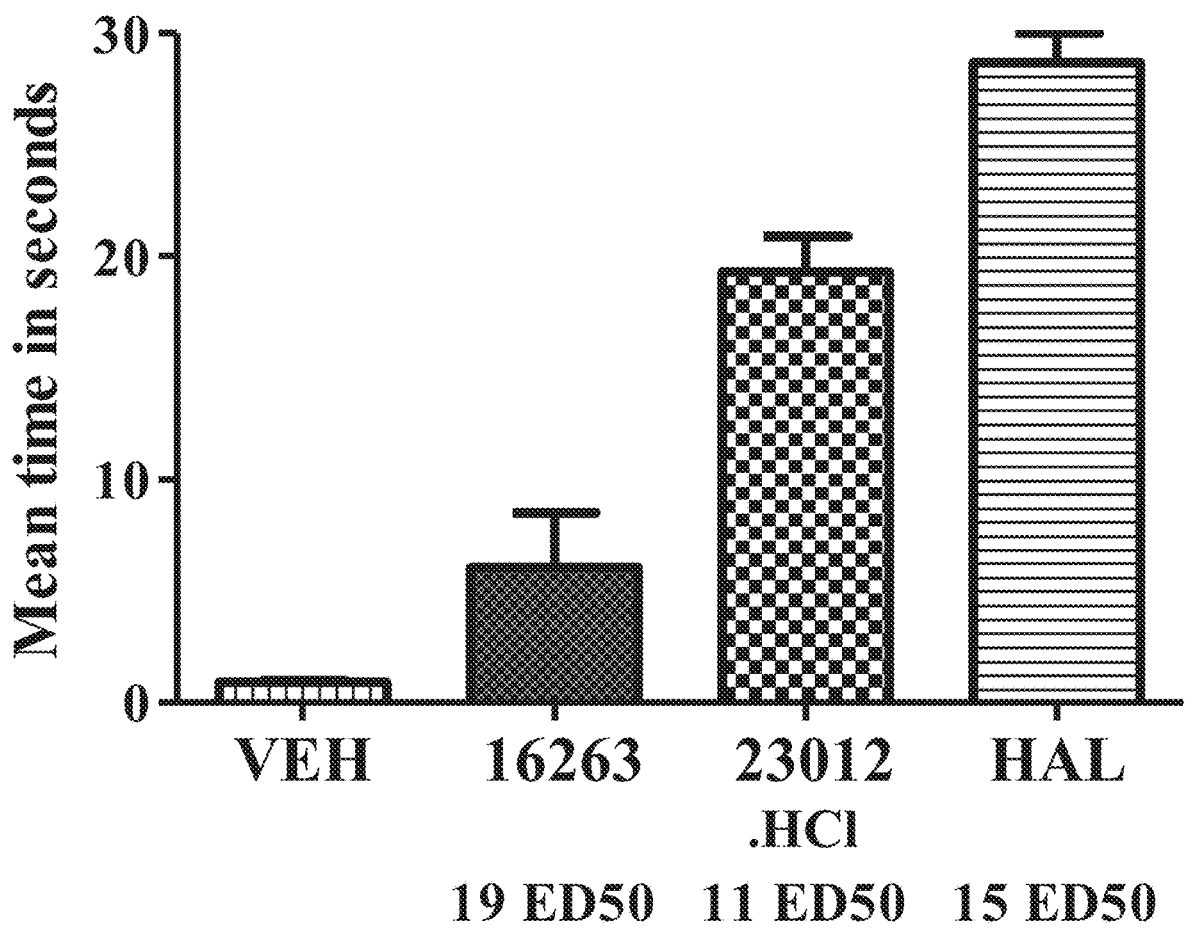
FIG. 10C depicts results of catalepsy bar test upon administration of higher doses of SYA16263. SYA23012, and haloperidol and tropane analogs.

Comparison of the antipsychotic and catalepsy potentials of SYA16263 and SYA23012(tropane analog), SYA23013 (tropane analog) and haloperidol can be seen in FIGS. 10A-10C. Structures of SYA16263, haloperidol, SYA23012 and SYA23013 can be seen in FIGS. 9A-9C.

TABLE 2

Preliminary structure-functional relationship evaluation.

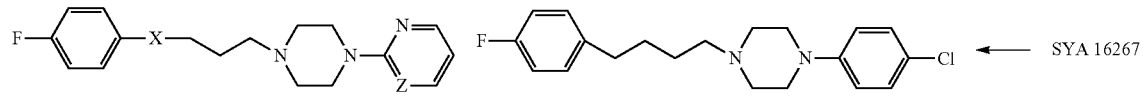

| | | | β-Arrestin | | cAMP | |
|---|---|---|---|---|---|---|
| Compound | X; Z | $D_2R$, $K_i$ (nM) | *$EC_{50}$ (nM) | $E_{max}$ (%) | $EC_{50}$ (nM) | $E_{max}$ (%) |
| Aripiprazole | — | 3.3 | 2.4 | 73.0 | 38.0 | 51.0 |
| SYA16263 | $CH_2$; CH | 124 ± 10 | 10.4 | 92.2 | 5.7 | 64.4 |
| SYA16264 | O; CH | 186 ± 16 | 40.4 | 75.7 | ND | ND |
| SYA16268 | $CH_2$; N | 269 ± 17 | 151 | 71.9 | ND | ND |
| SYA16267 | — | 284 ± 21 | 248 | 5.1 | ND | ND |
| SYA23013 | — | 27.0 ± 0.36 | 36.7 | 75.0 (Ant) | 299 | 75.0 (Ant) |

These results show that SYA16263 has agonist actions at both the G protein dependent and independent β-arrestin signaling pathways. Interestingly, its functional profile at the $D_2R$ mimics that of aripiprazole, albeit superior in its efficacy. For example, while it has only a moderate binding affinity to $D_2R$ [$K_i$=124 nM], SYA16263 is more potent and more efficacious as a partial agonist [$EC_{50}$=5.7 nM; $E_{max}$=64.4%] than aripiprazole [$EC_{50}$=38.0 nM; $E_{max}$=51.0%] at the $D_2R$. Also, while less potent, it is more efficacious in promoting recruitment of β-arrestin-2 to $D_2R$ [$EC_{50}$=10.4 nM; $E_{max}$=92%] than aripiprazole [$EC_{50}$=2.4 nM; $E_{max}$=73%].

Table 2 also reports preliminary structural modifications of SYA16263, the binding affinities ($K_i$ values) and abilities to recruit β-arrestin-2 to $D_2R$. The results suggest that the 1-(pyridin-2-yl)piperazine moiety plays a key role in β-arrestin recruitment to the $D_2R$. It is observed that replacement of the pyridine moiety with 4-CL-Phenyl moiety resulted in significant loss of the ability of SYA16267 to engage β-arrestin-2 mediated signaling at the $D_2R$. Overall, binding to the $D_2R$ correlates well with the $EC_{50}$ values of the compounds evaluated in engaging β-arrestin-2 mediated signaling at the $D_2R$. The recruitment of β-arrestin-2 to $D_2R$ explains the observed absence of catalepsy. On the other hand, SYA23013 does not have the ability to recruit β-ar- As can be seen in FIG. 10A, SYA16263, haloperidol and the tropane analogs each produced dose-dependent antipsychotic activity in animal models of schizophrenia. However, at 6×$ED_{50}$ values, SYA16263 demonstrated no catalepsy, while the tropane analogs and haloperidol produced significant catalepsy (FIG. 10B). Similar results were observed for the highest doses evaluated (19$ED_{50}$, 11$ED_{50}$, and 15$ED_{50}$ for SYA16263, SYA23012, and haloperidol, respectively) (FIG. 10C). The results are consistent with the fact that SYA16263 promotes $D_2$-mediated β-arrestin-2 translocation, while haloperidol and the tropane analogs act as antagonists at both the cAMP and β-arrestinergic signaling, do not recruit β-arrestin-2 to the $D_2R$, and therefore induce significant catalepsy in animals.

EXAMPLE 4

Evaluation of SYA16264

SYA16264 (Clog P=3.81) was synthesized at Florida A&M University with CHN values within 0.4% of theoretical values as determined by CHN analysis. The free bases were dissolved in filtered (0.22μ) 1% lactic acid vehicle for all animal studies.

All methodologies were performed as discussed above with reference to evaluation of SYA16263 in Example 1.

A. Effects of SYA16264 on Apomorphine-Induced Climbing (FIG. 7)

Figure 7:
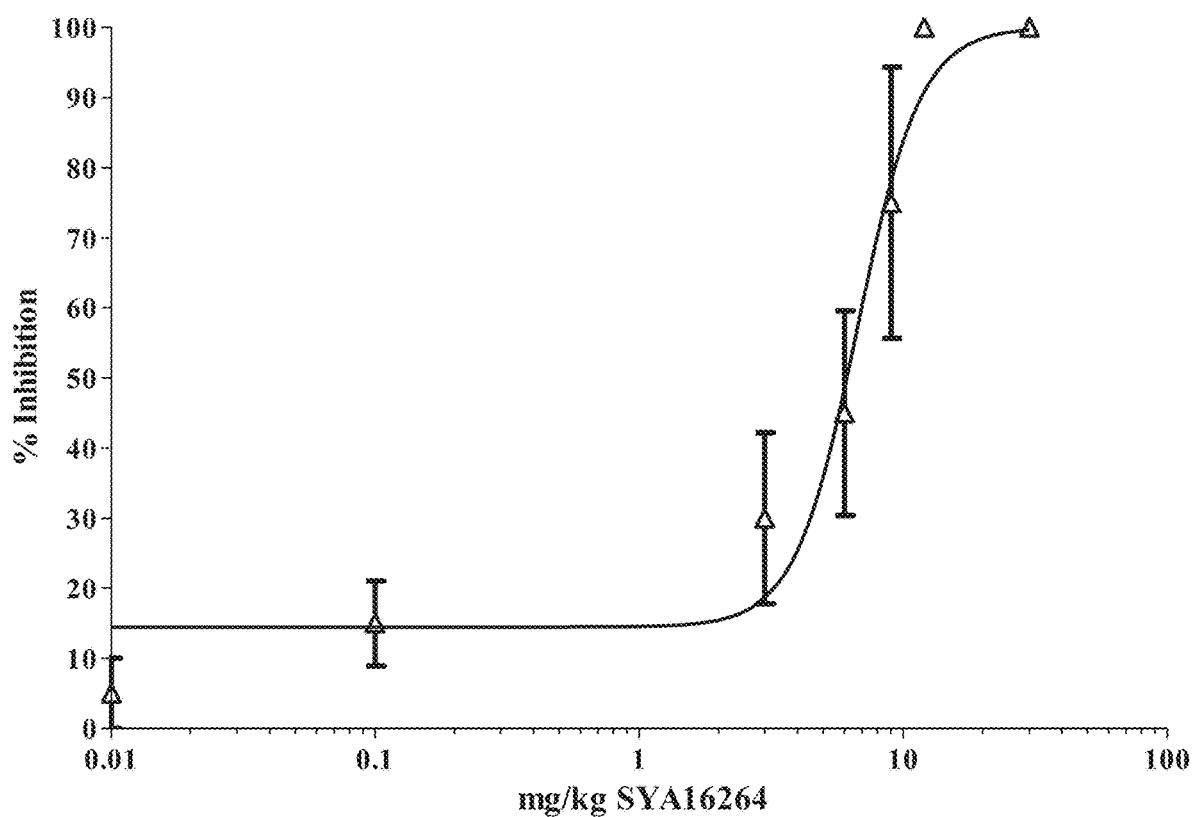
FIG. 7 shows that SYA16264 inhibited APO-induced climbing behavior in mice with an ip ED50 of 21.3 μmole/kg (6.73 mg/kg), n=5 mice/dose. Error bars are SEM.

SYA16264 reversed apomorphine-induced climbing behavior in mice in a dose-dependent manner as shown in FIG. 7, with an ip $ED_{50}$ of 21.3 µmole/kg (6.73 mg/kg). This indicates that SYA16264 may serve as an antipsychotic agent.

Figure 8:
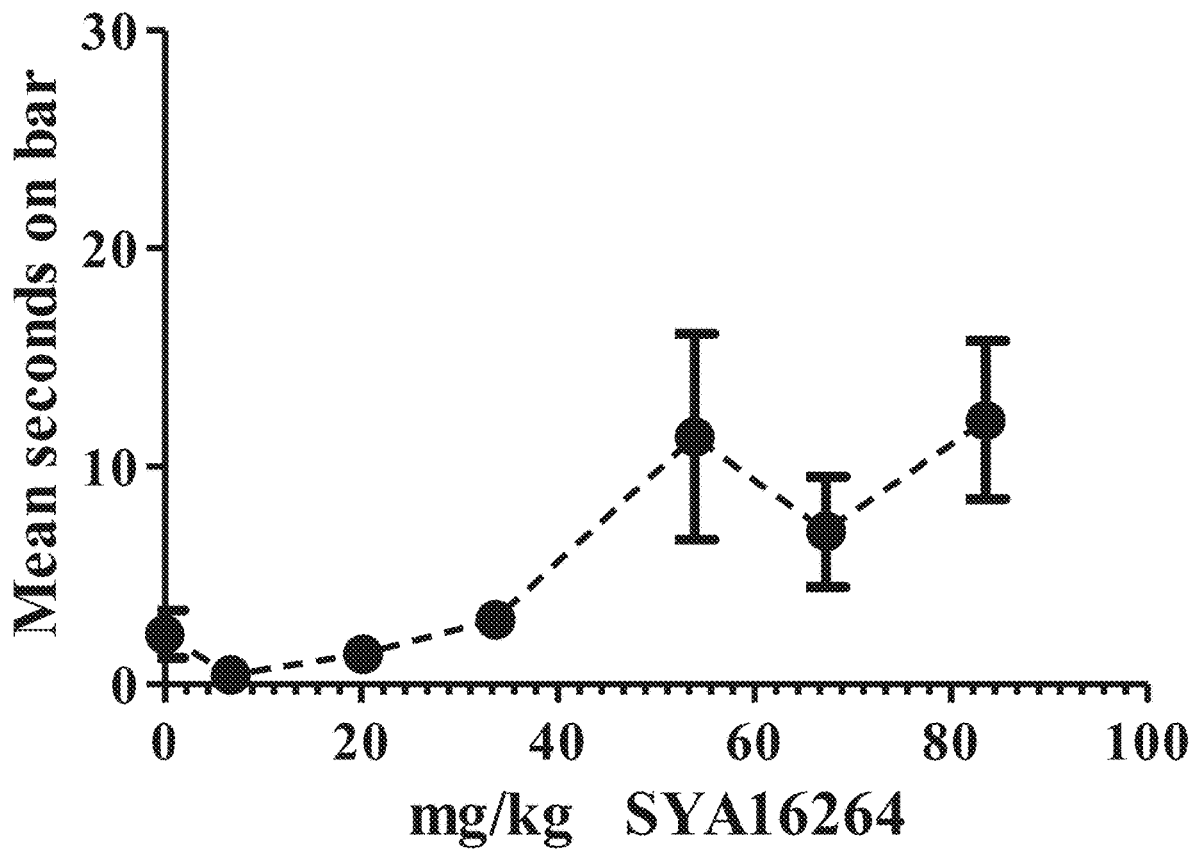
FIG. 8 shows that no bar catalepsy (mean <20 seconds on bar) was observed for up to 265 μmole/kg (83.5 mg/kg) SYA16264 (13×$ED_{50apom}$) n=5 rats/dose. Error bars are SEM.

B. Catalepsy Bar and CLP Tests (FIG. 8)

SYA16264 displayed no catalepsy (mean time on bar <20 seconds) up to $13 \times ED_{50apom}$ (265 µmole/kg or 83.5 mg/kg). Testing stopped at solubility limit. Catalepsy $AED_{50} > 83.5$ mg/kg. No catalepsy was detected with the CLP test with 0-5 s response for all doses up to 83.5 mg/kg. All rats righted themselves in the sedation test following catalepsy testing.

D4 Receptors

In certain embodiments, the current invention includes selective dopamine D4 agonists that may treat erectile dysfunction or cognitive symptoms in schizophrenia or the elderly. Dopamine D4 receptors have been shown to play key roles in certain CNS pathologies including erectile dysfunction, reversal of cognitive deficits and addiction to cigarette smoking. Thus, selective D4 ligands may be useful in treating some of these conditions. Previous studies by the current inventors have indicated that the piperazine analog of haloperidol exhibits selective and increased affinity to the $DAD_4$ receptor subtype, in comparison to its piperidine analog. As such, a haloperidol scaffold was developed—according to K. Peprah, et al. Multi-receptor drug design: Haloperidol as a scaffold for the design and synthesis of atypical antipsychotic agents, Bioorg Med Chem. 2012 Feb. 1; 20(3):1291-7, doi: 10.1016/j.bmc.2011.12.019. Epub 2011 Dec. 22—to provide a base molecule on which functional groups were tested to identify agents.

Figure 11:
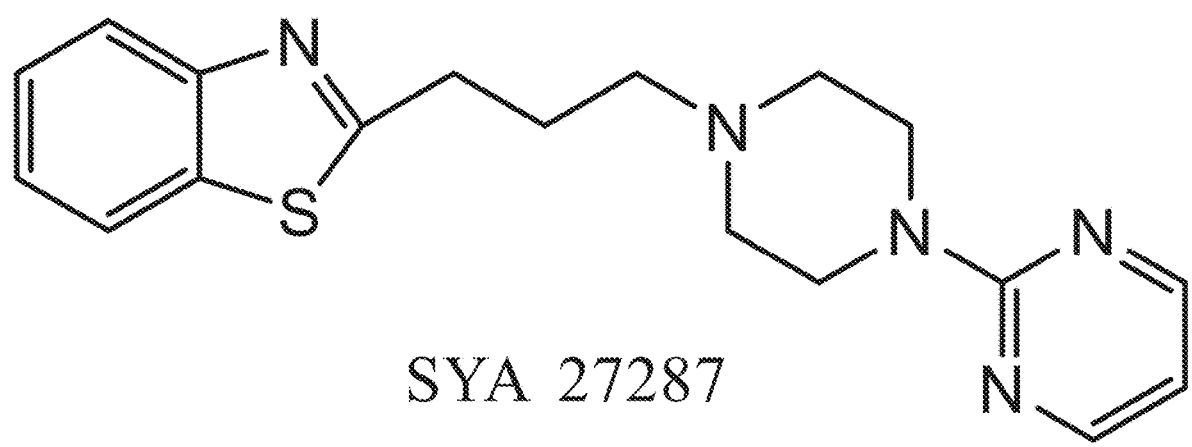
FIG. 11 depicts the structure of SYA27287.

Due to the piperazine analog of haloperidol exhibiting selective and increased affinity to the $DAD_4$ receptor subtype, the piperazine moiety was explored further to identify new agents that are selective at the D4 receptor. Compound 27 ($K_iD_4$=0.84 nM) was the most potent of the compounds tested. However, it only had moderate selectivity for the $D_4$ receptor. Compound 28 [SYA27287; (2-(3-(4-(Pyrimidin-2-yl)piperazin-1-yl)propyl)benzo[d]thiazole trihydrobromide); $K_iD_4$=3.9 nM; FIG. 11] was more discriminatory for the D4 receptor subtype, though not as potent. In fact, SYA27287 has little or no binding affinity to any of the other four DA receptor subtypes.

In addition, of the 23 CNS receptors evaluated, only two—$5HT_{1A}R$ and $5HT_{2B}R$—have binding affinity constants better than 100 nM ($K_i$<100 nM). SYA27287 was also evaluated for intrinsic activity and it was revealed to be acting as a D4 agonist ($E_{max}$=117%; $EC_{50}$=660 nM). Thus, SYA27287 and its analogs are observed to be useful D4-selective agonists that have utility in reversing cognitive deficits in schizophrenia and in treating male erectile dysfunction. Certain aspects of this research are further described in the inventors' previous work, specifically Sampson D. et al., "Identification of a New Selective Dopamine D4 Receptor Ligand", Bioorg Med Chem. 2014 Jun. 15; 22(12):3105-14. doi: 10.1016/j.bmc.2014.04.026. Epub 2014 Apr. 20.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of recruiting β-arrestin to D2 dopamine receptors in a subject, comprising:
   administering to the subject, via intraperitoneal injection, a composition comprising
   at least 50 mg/kg of an SYA16263 compound; and
   a pharmaceutically acceptable carrier;
   wherein the SYA16263 compound in the composition selectively recruits β-arrestin to D2 dopamine receptors, such that the subject is substantially free of extrapyramidal symptoms upon the administration of the SYA16263 compound of the composition.

2. A method as in claim 1, wherein the subject suffers from schizophrenia.

* * * * *